US00PP28718P3

(12) United States Plant Patent
Olesen

(10) Patent No.: US PP28,718 P3
(45) Date of Patent: Dec. 5, 2017

(54) GROUND COVER ROSE PLANT NAMED 'POULTC023'

(50) Latin Name: ***Rosa* hybrid**
Varietal Denomination: Poultc023

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 153 days.

(21) Appl. No.: 14/756,249

(22) Filed: Aug. 20, 2015

(65) Prior Publication Data

US 2017/0055383 P1 Feb. 23, 2017

(51) Int. Cl.
*A01H 5/02* (2006.01)

(52) U.S. Cl.
USPC ..... Plt./108

(58) Field of Classification Search
USPC ..... Plt./101, 102, 108
See application file for complete search history.

(56) References Cited

PUBLICATIONS

Poulsen Roser A/S website. http://de.poulsenroses.eu/sortiment/rosen-collectionen/towne-country/real-cover.aspx. accessed Mar. 16, 2017. 1 page.*

* cited by examiner

*Primary Examiner* — Susan McCormick Ewoldt
*Assistant Examiner* — Karen Redden

(57) ABSTRACT

A new garden rose plant of the Ground Cover class which has abundant, red flowers and attractive foliage. This new and distinct variety has shown to be uniform and stable in the resulting generations from asexual propagation.

2 Drawing Sheets

Botanical designation: *Rosa* hybrid.
Variety denomination: 'Poultc023'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poultc023', originated as a single seedling from the stated cross.

The new variety may be distinguished from its male pollen parent and female seed parent primarily by the following characteristics. The male pollen parent has apricot colored flowers, while the new variety has red flowers. The female seed parent has smaller flowers than the new variety.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poultc023' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poultc023' was selected in the spring of 2008 by the inventor as a single plant from the progeny of the aforementioned hybridization.

Asexual reproduction of 'Poultc023' by traditional budding and rooted cuttings was first done by Mogens N. Olesen in the nursery in Fredensborg, Denmark in July, 2008. This initial and other subsequent asexual propagations conducted in controlled environments have demonstrated that the characteristics of 'Poultc023' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poultc023'.

Specifically illustrated in FIG. 2 are a cluster of unopened flower buds, flower petals detached, reproductive flower parts, detached sepals, a fully opened flower, and other flowers at various stages of their development.

DETAILED DESCRIPTION OF THE VARIETY

Figure 1:
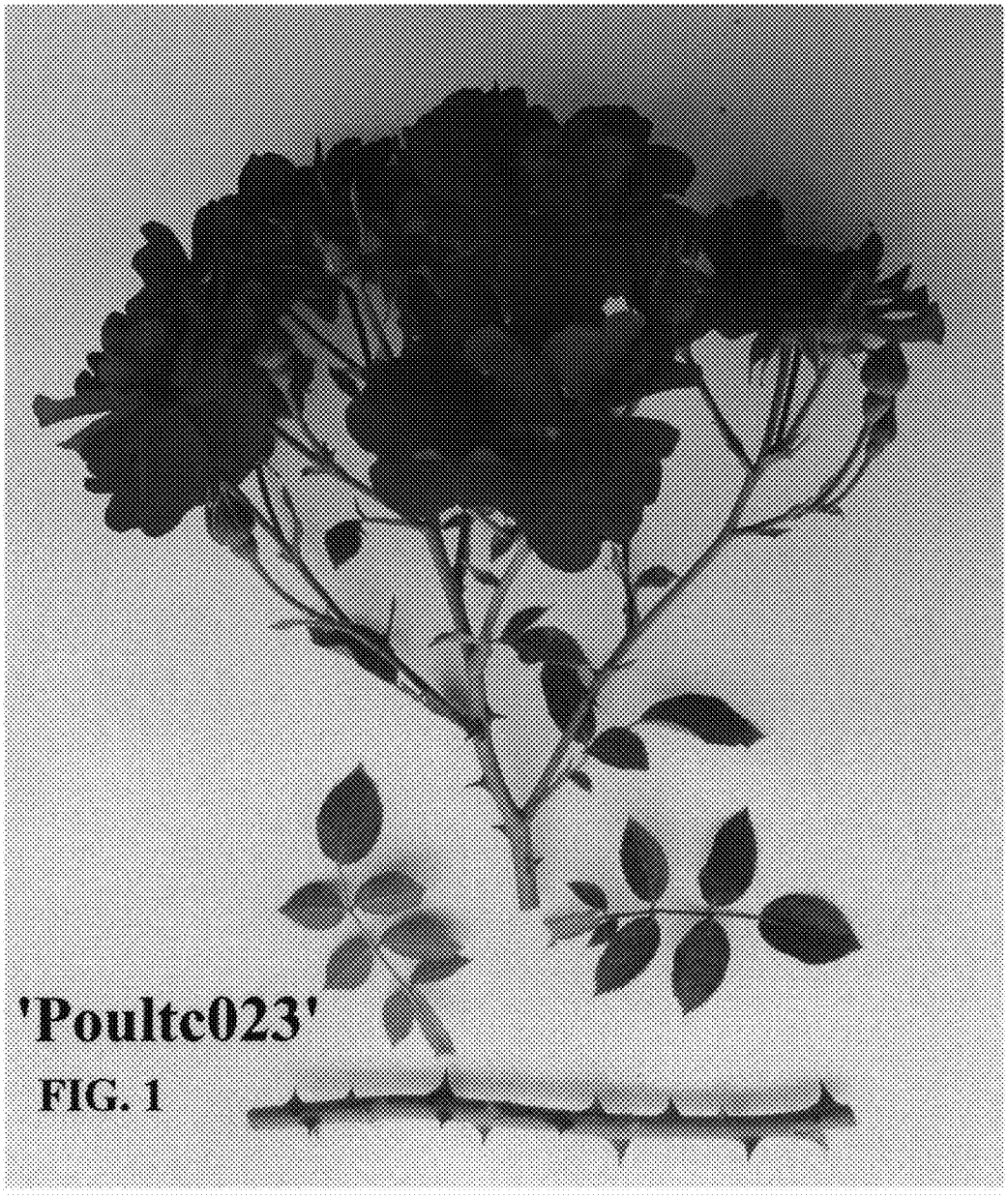
FIG. 1 shows a cluster of fully opened flowers as it appears on a branch, peduncles, a bare branch exhibiting prickles, and leaves. Plants shown are 2 years of age.
Figure 2:
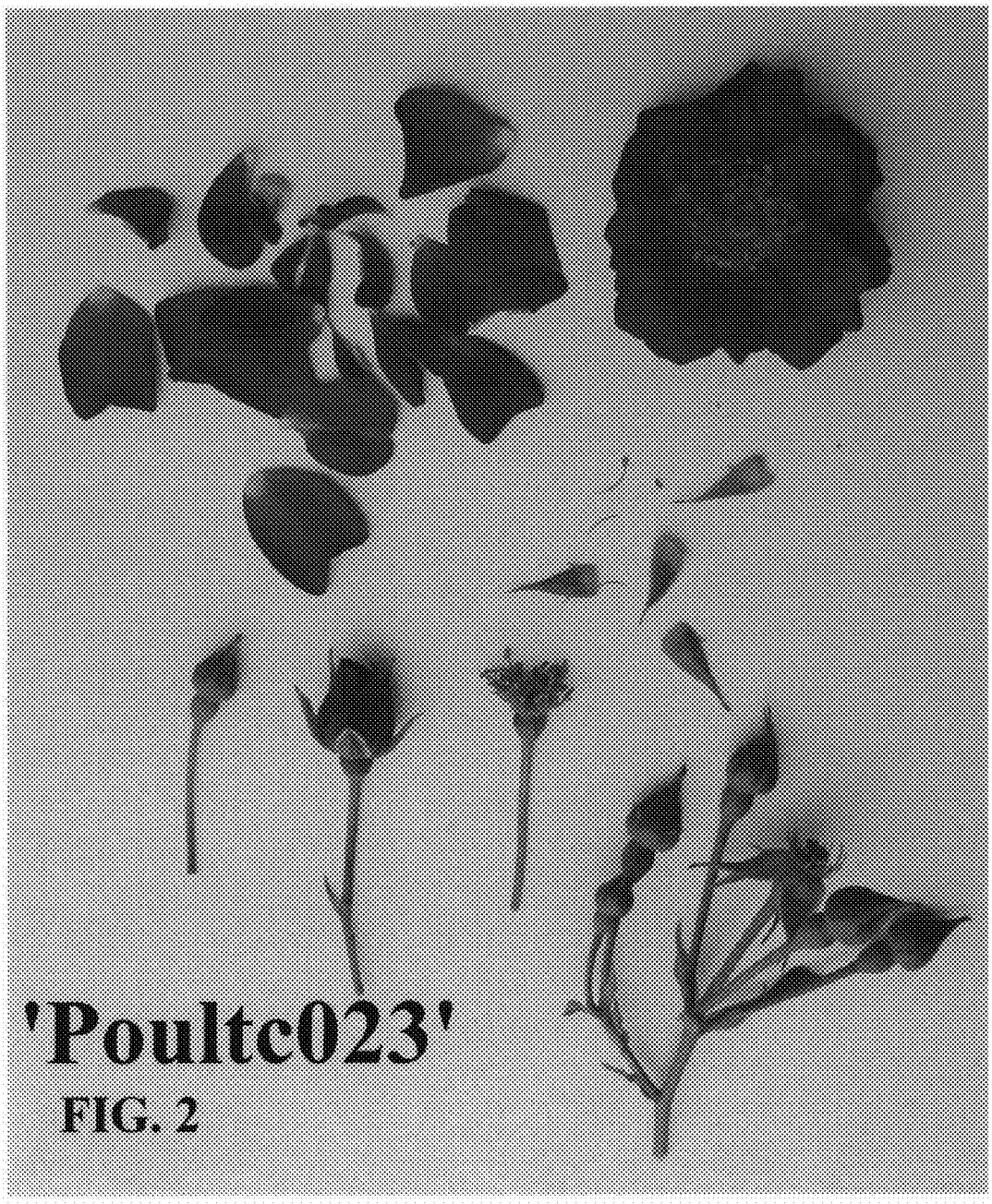

The following is a description of 'Poultc023', as observed in its growth in in a field nursery in Marion County, Oreg.

Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulharmu', U.S. Plant Pat. No. 12,681 are compared to 'Poultc023' in Chart 1, below:

| | 'Poultc023' | 'Poulharmu' |
|---|---|---|
| Petal Count | 20 | 14-16 petals |
| Flower Diameter | 65 mm | 45 mm |
| General Tonality of Flower Color | Red Group 46A | Red Group 44 |

Flower and Flower Bud

Blooming habit: Continuous.

Flower bud:

*Size*.—Upon opening, about 20 mm in length from base of receptacle to end of bud. Bud diameter is 9 mm.

*Bud form*.—Ovoid.

*Bud color*.—As sepals divide petals are Red Group 46A.

*Sepal inner surface*.—Color: Yellow-Green Group 145B. Surface: Lightly pubescent.

*Sepal outer surface*.—Color: Yellow-Green Group 144A with intonations of Greyed-Purple Group 183A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—15 mm long, 6 mm wide.

*Receptacle*.—Texture: Smooth. Size: About 6 mm in height, 6 mm wide. Color: Yellow-Green Group 144A with intonations of Greyed-Purple Group 183A. Shape: Elliptic.

*Pedicel*.—Surface: Smooth. Length: About 23 mm. Diameter: 2 mm. Color: Yellow-Green Group 144A. Strength: Moderate to weak.

*Peduncle*.—Length: Ranging from 3 to 10 cm. Diameter: 3 mm. Color: Yellow-Green Group 145A. Texture: Smooth.

Flower bud development: Flower buds are borne in panicles consisting of 15 to 30 flower buds per flowering stem.

Flower bloom:

*Fragrance*.—Moderate, old rose scent.

*Duration*.—The blooms have a duration on the plant of approximately 8 days. Petals fall cleanly away from plant after flowers have fully matured.

*Size*.—Flower diameter is about 65 mm when fully open. Flower depth is about 18 mm.

*Flower shape*.—Open cup, semi double.

Shape of flower, side view: The upper portion is a flat convex. The lower portion is concave.

Petalage: Under normal conditions, flowers have 20 petals total, 3 of which are petaloids.

General tonality of flower: Open flowers are Red Group 46A.

Petal color:

*Upper surface*.—Red Group 46A.

*Lower surface*.—Red-Purple Group 59C with occasional streaks White Group N155A.

*Petal base*.—Upper and lower surface is a spot of Yellow Group 4D.

Petals:

*Petal reflex*.—Flat.

*Margin*.—Entire and uniform. Moderate undulations.

*Shape*.—Elliptic with a broad apex. Apex shape: Rounded. Base shape: Acute.

*Size*.—25 mm (l)×22 mm (w).

*Texture*.—Smooth.

*Thickness*.—Thin.

Petaloids:

*Size*.—About 10 mm (l) by 5 mm (w).

*Quantity*.—3 on average.

*Shape*.—Asymmetric, crescent shaped.

*Color*.—The upper surface is Red Group 46A. The lower surface is Red-Purple Group 59C. Base of petaloid is Yellow Group 4D.

Reproductive flower parts:

*Pollen*.—None observed.

*Anthers*.—Size: 1 mm in length. Color: Yellow-Orange Group 14C. Quantity: 45 on average.

*Filaments*.—Color: Orange-Red Group 34C. Length: 5 mm.

*Pistils*.—Length: 2 mm. Quantity: 20 on average.

*Stigmas*.—Color: Greyed-Yellow Group 162D.

*Styles*.—Color: Greyed-Purple Group 187A.

*Location of stigmas*.—Inferior in location relative to the length of the filaments and the height of the anthers.

*Hips*.—None Observed.

Plant

Plant growth: Upright, bushy. Plants are about 55 cm in height, and 65 cm wide.

Stems:

*Color*.—Juvenile growth: Yellow-Green Group 144B. Mature growth: Yellow-Green Group 144A.

*Length*.—On average, canes are 40 cm from the base of the plant to the flowering portion.

*Diameter*.—7 mm.

*Internodes*.—On mature canes about 30 mm between nodes.

*Surface texture*.—Young wood: Smooth. Older wood: Smooth.

Long prickles:

*Incidence*.—15 prickles per 10 cm of stem.

*Size*.—Average length of prickles on mature stems is 6 mm.

*Shape*.—Upper and lower portion of prickles are concave.

*Color*.—Juvenile prickles: Greyed-Purple Group 181B. Mature prickles: Greyed-Orange Group 168D.

Plant foliage:

*Compound leaf*.—About 85 mm (l)×60 (w).

*Quantity*.—3 leaves per 10 cm of stem on average.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: 20 mm long, 5 mm wide. Quantity: 2 per compound leaf. Shape: Linear, slightly broad based with outward extending apices. Margins: Finely serrated. Color: Yellow-Green Group 144A.

*Petiole*.—Length: 20 mm. Diameter: 1.5 mm.

*Upper surface*.—Color: Yellow-Green Group 144A.

*Lower surface*.—Color: Yellow-Green Group 144B.

*Rachis*.—Length: 25 mm. Upper surface: Color: Yellow-Green Group 144A. Lower surface: Color: Yellow-Green Group 144B.

*Leaflet*.—Quantity: Normally 7 leaflets. Margins: Serrated. Size: On average terminal leaflets are 35 mm long, 20 mm wide. Shape: Generally elliptical. Base: Rounded. Apex: Acuminate. Texture: Smooth. Thickness: Average. Arrangement: Odd pinnate. Venation: Reticulate. Glossiness: Very glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the Ground Cover rose class named 'Poultc023', substantially as illustrated and described herein, due to its abundant red flowers, disease resistance, and extended period of bloom.

* * * * *

'Poultc023'